United States Patent [19]
Ponsford et al.

[11] Patent Number: 6,018,085
[45] Date of Patent: Jan. 25, 2000

[54] METHOD OF RECLAIMING STYRENE AND OTHER PRODUCTS FROM POLYSTYRENE BASED MATERIALS

[76] Inventors: Thomas E. Ponsford; Henry T. Ponsford, both of P.O. Box 1256, Poway, Calif. 92074

[21] Appl. No.: 09/150,603

[22] Filed: Sep. 10, 1998

Related U.S. Application Data

[60] Provisional application No. 60/058,574, Sep. 11, 1997.

[51] Int. Cl.$^7$ ........................................................ C07C 1/00
[52] U.S. Cl. ............................................ 585/241; 585/240
[58] Field of Search ..................... 585/241, 240; 201/2.5, 25

[56] References Cited

U.S. PATENT DOCUMENTS

| | | |
|---|---|---|
| 2,372,527 | 3/1945 | Soday . |
| 2,372,528 | 3/1945 | Soday . |
| 2,383,922 | 8/1945 | Soday . |
| 3,692,858 | 9/1972 | Brewer et al. . |
| 3,829,558 | 8/1974 | Banks et al. ............................. 423/481 |
| 3,985,820 | 10/1976 | Albright et al. . |
| 4,250,158 | 2/1981 | Solbakken et al. ...................... 423/499 |
| 4,375,570 | 3/1983 | Yudovich . |
| 5,136,117 | 8/1992 | Paisley et al. ........................... 585/241 |
| 5,288,934 | 2/1994 | de Broqueville . |
| 5,406,010 | 4/1995 | Ponsford et al. . |
| 5,502,263 | 3/1996 | Ponsford et al. ....................... 585/241 |
| 5,672,794 | 9/1997 | Northemann . |
| 5,821,396 | 10/1998 | Bouziane ................................ 585/241 |

*Primary Examiner*—Bekir L. Yildirim
*Attorney, Agent, or Firm*—Foley & Lardner

[57] ABSTRACT

A method of reclaiming styrene from polystyrene-containing materials contaminated with animal fats and/or vegetable oils. A solution of polystyrene from such materials in a solvent is heated in distillation equipment to depolymerize the polystyrene and produce a styrene fraction and a heavier fraction, the styrene fraction being separated from the heavier fraction. Prior to heating, an inert gas is used to purge the distillation equipment of oxygen. The method preferably is carried out at the lowest temperature which will achieve the desired rate of depolymerization.

10 Claims, No Drawings

METHOD OF RECLAIMING STYRENE AND OTHER PRODUCTS FROM POLYSTYRENE BASED MATERIALS

This application is based on and claims the benefit of provisional application No. 60/058,574, filed Sep. 11, 1997.

BACKGROUND OF THE INVENTION

1. Field of the Invention

This invention relates to a method of reclaiming styrene and other products from polystyrene-based materials. In particular, the method of the invention reduces the quantity of contaminants formed during depolymerization of the polystyrene in the recovered product.

2. Description of Related Art

In the specification of U.S. Pat. No. 5,502,263 (the '263 patent), the statement was made that "some contaminants, such as certain vegetable oils, interfere with satisfactory operation of the invention . . ." (col. 13, lines 13–15). This cited interference arose from the dissociation of the contaminant oils at polystyrene depolymerization temperatures. The resultant contaminants are free fatty acids and possibly orthoxylene, which are difficult, but not impossible, to separate from the desired styrene monomer and styrene oil during fractional distillation after depolymerization. Pure mineral oil was not found to be a problem in the early work.

SUMMARY OF THE INVENTION

The inventors have conducted additional research since the application which matured into the '263 patent was filed. The inventors have discovered improvements to the method of the '263 patent which essentially prevent the formation of the objectionable byproducts. This new research addressed contamination both from typical vegetable oils and from typical animal fats. The improvements greatly enhance the commercial application and value of the improved invention compared with the invention of the cited patent.

The improvement is to a method of reclaiming styrene from polystyrene-containing materials, comprising the steps of heating in distillation equipment, under controlled conditions, a solution of polystyrene from such materials in a solvent to depolymerize the polystyrene and produce a styrene fraction and a heavier fraction; and separating the styrene fraction from the heavier fraction. The improvement comprises purging the distillation equipment with an inert gas to substantially purge oxygen therefrom prior to the step of heating the polystyrene solution.

In another aspect of the above-described method, the heating step is carried out at the lowest temperature which will achieve the desired rate of depolymerization.

DETAILED DESCRIPTION OF A PREFERRED EMBODIMENT

The first improvement to the method of the '263 patent, which is incorporated herein by reference, is the total purging of air from the distillation equipment prior to heating. It was believed that, when practicing the method of the '263 patent, the presence of some air in the equipment would not adversely affect the continuing process. Rather, it was believed that the initial distilled vapors would sweep all of the air from the distillation equipment before a significant degree of oxidation of styrene, styrene oil, or polystyrene occurred. These oxidation products interfere with depolymerization of the polystyrene.

The inventors have now discovered, however, that substantially complete purging of air before a significant degree of oxidation has begun has remarkable effects during the entire process. The careful use of an inert purging gas, such as carbon dioxide, nitrogen, argon, or steam, causes several beneficial results throughout the entire process. Carbon dioxide is particularly beneficial. An "inert" purging gas in the context of this invention means any non-oxidizing purging gas which will sweep away substantially all oxygen from the distillation equipment prior to heating and not adversely affect the depolymerization process.

The first observable effect is the lowering of the temperature of depolymerization from the previous range of 355–370° C. to 315–330° C., while still maintaining a time rate of depolymerization useful for commercial application. Depolymerization will occur at temperatures below 300° C., but not generally at a commercially acceptable rate.

A second observable effect is a marked decrease in coloration of the mixed distillates. Typically, for product produced in accordance with the method of the '263 patent, with no oil contamination of the feedstock, no purging of air, and a depolymerization temperature about 370° C., the first 20% of the distillate was very light yellow; at 50%, it was yellow; at 75%, it was orange; and the last 25% was reddish-orange. With oil contamination added, the same development of color occurred, but later in the process, and the product was lighter at the end. Although the inventors do not wish to be bound by theory, it is believed that fats and oils are oxidized more easily than styrene-containing moieties, and so reduce the amount of oxygen available to oxidize styrene, styrene oil, or polystyrene. In both of these examples, the coloration had no turbidity. With or without oil contamination, but with inert gas purging and depolymerization temperature about 320° C., the entire distillate was water-clear. This decrease in coloration is a clear indication that contamination of the distillate has been greatly reduced.

A third observable effect is the absence of any detectable odor of butyric acid or acrolein in the improved distillate from samples containing oil contamination. These substances are organic compounds formed from the thermal breakdown of edible fats and oils, and have sharp, easily identifiable odors. Butyric acid also has a boiling point close to that of the desired styrene monomer.

The second improvement over the method of the '263 patent is careful control of the depolymerization temperature to the lowest temperature which will achieve the desired rate of depolymerization. This careful temperature control takes advantage of the observed lower effective depolymerization temperature created by inert gas purging to improve the purity of the distillates.

Several published investigations of the relative amounts of fats and oils present in contaminated food service foam trash have reported that contaminated trash which has been washed in cold water without detergents retains about 3% oils by weight, based on the weight of the trash. The inventors' independent tests revealed that foam trash which was forcibly immersed in oils overnight, then washed in cold water without detergents, retained about 4% of oils by weight. In the case of actual trash, some pieces have not been washed at all, but others have not been contaminated. To ensure that the method of the invention works on feedstocks heavily contaminated with oils, the inventors tested specimens with 5% to 7% total oils and fats, by weight, added to the cooker. The contaminants included vegetable oils such as corn oil, soybean oil, and canola oil; animal fats such as pig lard and beef tallow; and both types of contaminants together.

Analyses of the improved distillates obtained in accordance with the method of the invention were made by an independent commercial chemical analysis laboratory, using mass spectrography and gas chromatography. In particular, the gas chromatography was performed using a special polar column capable of making precise distinctions between styrene monomer and other chemicals such as certain free fatty acids and orthoxylene, which have boiling points close to that of styrene monomer. Therefore, these contaminants are difficult to separate from desired styrene monomer by distillation.

These laboratory tests have identified a number of favorable differences between the original and the improved distillates. The production of both the desirable styrene monomer and the desirable light styrene oil have been increased by several percent using careful purging. The production of heavy styrene oil has been similarly decreased, and tar production has been clearly reduced. Most importantly, the presence of free fatty acids with boiling points near that of styrene monomer and the three variants of xylene were all below a detection level of 0.01%. The elimination of these chemicals is particularly significant, since their boiling temperatures near that of styrene monomer make separation from styrene monomer by fractional distillation difficult. The results of a typical analysis are shown in Table 1.

EXAMPLE

The cooker was carefully cleaned with Methyl Ethyl Ketone and dried. Then, the following were placed in the unheated cooker:

250 grams of commercial polystyrene;

7.5 grams of pig lard;

2.5 grams of corn oil; and 3.0 grams of soybean oil.

This feedstock thus comprised 5.2% contaminants by weight, based on the weight of the polystyrene. Then, the entire system was purged with a quantity of $CO_2$ sufficient to purge essentially all oxygen from the system.

Depolymerization then was carried out in accordance with the method disclosed herein; the temperature during depolymerization varied from 310° C. to 330° C.

TABLE 1

Laboratory Analysis of Depolymerization Distillates

| Contaminant | Concentration |
| --- | --- |
| meta-Xylene | Less than 100 ppm by wt (0.01%) |
| para-Xylene | Less than 100 ppm by wt (0.01%) |
| ortho-Xylene | Less than 100 ppm by wt (0.01%) |
| Free fatty acids detected near the B.P. of styrene monomer | None |

The improvements over the process of the '263 patent therefore make the production of commercially pure (99.95%) styrene monomer from polystyrene trash contaminated by typical vegetable oils and animal fats routinely practical in current state-of-the art fractional distillation columns, and negate the interference described in the '263 patent.

It will be apparent to those skilled in the art that various modifications to the above-described preferred embodiment may be made without departing from the true spirit and scope of the invention, which is to be limited only by the appended claims.

We claim:

1. A method of reclaiming styrene from polystyrene-containing materials mixed with contaminants comprising at least one selected from the group consisting of animal fats, vegetable oils and blends thereof, the method comprising the steps of:

mixing the polystyrene-containing materials with a solvent to form a solution of polystyrene and contaminants from said materials in said solvent, placing said polystyrene solution in distillation equipment, purging the distillation equipment with an inert gas to substantially purge oxygen therefrom, heating said polystyrene solution in the distillation equipment, under controlled conditions, to depolymerize the polystyrene and produce a styrene fraction and a heavier fraction, and separating the styrene fraction from the heavier fraction.

2. The method of claim 1, wherein said inert gas is selected from the group consisting of carbon dioxide, nitrogen, argon, and steam, and blends thereof.

3. The method of claim 1, wherein the step of heating said polystyrene solution is carried out at the lowest temperature which will achieve the desired rate of depolymerization.

4. The method of claim 1, wherein said solvent is selected from the group consisting of styrene, and styrene oil resulting from the partial depolymerization of polystyrene, and blends thereof.

5. The method of claim 3, wherein the step of heating said polystyrene solution is carried out at a temperature in the range of approximately 300° C. to 350° C.

6. The method of claim 5, wherein the step of heating said polystyrene solution is carried out at a temperature in the range of approximately 310° C. to 340° C.

7. The method of claim 6, wherein said inert gas is selected from the group consisting of carbon dioxide, nitrogen, argon, and steam, and blends thereof.

8. A method of reclaiming styrene from polystyrene-containing materials mixed with contaminants comprising at least one selected from the group consisting of animal fats, vegetable oils and blends thereof, the method comprising the steps of:

mixing the polystyrene-containing materials with a solvent selected from the group consisting of styrene, and styrene oil resulting from the partial depolymerization of polystyrene, and blends thereof, to form a solution of polystyrene from said materials in said solvent, placing said polystyrene solution in distillation equipment, purging the distillation equipment with an inert gas to substantially purge oxygen therefrom, heating said polystyrene solution in the distillation equipment, under controlled conditions, to depolymerize the polystyrene and produce a styrene fraction and a heavier fraction containing styrene oil as a result of the partial depolymerization of the polystyrene, said heating being carried out at the lowest temperature which will achieve the desired rate of depolymerization, separating the styrene fraction from the heavier fraction, and recycling at least a portion of said styrene oil to provide at least a portion of said solvent in the step of mixing the polystyrene-containing materials with a solvent prior to heating.

9. The method of claim 8, wherein the step of heating said polystyrene solution is carried out at a temperature in the range of approximately 310° C. to 340° C.

10. The method of claim 9, wherein said inert gas is selected from the group consisting of carbon dioxide, nitrogen, argon, and steam, and blends thereof.

* * * * *